United States Patent [19]
Robinson

[11] Patent Number: 5,854,275
[45] Date of Patent: Dec. 29, 1998

[54] CYCLIC IMIDE DERIVATIVES

[75] Inventor: Ralph P. Robinson, Gales Ferry, Conn.

[73] Assignee: Pfizer Inc., New York, N.Y.

[21] Appl. No.: 855,023

[22] Filed: May 13, 1997

Related U.S. Application Data

[60] Provisional application No. 60/007,580, May 16, 1996.
[51] Int. Cl.$^6$ .......................... A61K 31/40; C07D 209/56
[52] U.S. Cl. .......................... 514/411; 514/278; 514/292; 514/293; 514/300; 514/414; 514/417; 578/431; 578/433; 578/451; 578/473; 546/16; 546/82; 546/84; 546/113
[58] Field of Search .................................. 546/16, 82, 84, 546/113; 548/431, 433, 451, 473; 514/292, 293, 300, 411, 414, 417, 278

[56] References Cited

U.S. PATENT DOCUMENTS 5,455,258  10/1995  MacPherson ............................ 514/357

FOREIGN PATENT DOCUMENTS 606046  7/1994  European Pat. Off. .
9005719  5/1990  WIPO .

OTHER PUBLICATIONS

Brown FK et al. J. Med. Chem. 37, 674–688, 1994.

*Primary Examiner*—Evelyn Huang
*Attorney, Agent, or Firm*—Peter C. Richardson; Paul H. Ginsburg; Jolene W. Appleman

[57] ABSTRACT

The invention relates to a compound of the formula I

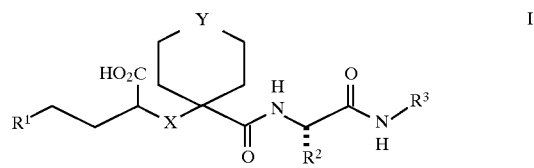

wherein $R^1$ is a cyclic imide group and X, Y, $R^2$, and $R^3$ are as defined herein. The invention further relates to pharmaceutical compositions containing, and methods of using, compounds of the formula I. Compounds of the formula I are useful in the treatment of diseases related to the production of matrix metalloproteinases and tumor necrosis factor.

11 Claims, No Drawings

CYCLIC IMIDE DERIVATIVES

This application claims the benefit of provisional application No. 60/007,580, filed May 16, 1996.

BACKGROUND OF THE INVENTION

The present invention relates to cyclic imide derivatives of the formula I that inhibit the production of matrix metalloproteinases. Metalloproteinases are effector molecules responsible for the degradation of the extensive extracellular matrix that makes up a large proportion of articular cartilage. The impairment or loss of joint function associated with osteoarthritis and rheumatoid arthritis is primarily due to the loss of articular cartilage. As inhibitors of the production of metalloproteinases, the cyclic imide derivatives of the formula I are useful in the treatment of a condition selected from the group consisting of arthritis, cancer, tissue ulceration, restenosis, periodontal disease, epidermolysis bullosa, scleritis and other diseases characterized by matrix metalloproteinase activity, AIDS, sepsis, septic shock and other diseases involving the production of TNF.

This invention also relates to a method of using such compounds in the treatment of the above diseases in mammals, especially humans, and to the pharmaceutical compositions useful therefor.

There are a number of enzymes which effect the breakdown of structural proteins and which are structurally related metalloproteases. Matrix-degrading metalloproteinase, such as gelatinase, stromelysin and collagenase, are involved in tissue matrix degradation (e.g. collagen collapse) and have been implicated in many pathological conditions involving abnormal connective tissue and basement membrane matrix metabolism, such as arthritis (e.g. osteoarthritis and rheumatoid arthritis), tissue ulceration (e.g. corneal, epidermal and gastric ulceration), abnormal wound healing, periodontal disease, bone disease (e.g. Paget's disease and osteoporosis), tumor metastasis or invasion, as well as HIV-infection (*J. Leuk. Biol.*, 52 (2): 244–248, 1992).

Tumor necrosis factor is recognized to be involved in many infectious and auto-immune diseases (W. Friers, *FEBS Letters*, 1991, 285, 199). Furthermore, it has been shown that TNF is the prime mediator of the inflammatory response seen in sepsis and septic shock (C. E. Spooner et al., *Clinical Immunology and Immunotathology*, 1992, 62 S11).

SUMMARY OF THE INVENTION

The present invention relates to compounds of the formula I

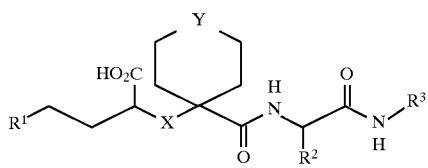

wherein

X is $CH_2$ or NH;

Y is a bond, $CH_2$, $CH((C_1-C_6)alkyl)$, $CF_2$, S, or O;

$R^1$ is an optionally substituted cyclic imide wherein the cyclic imide ring system has the formula

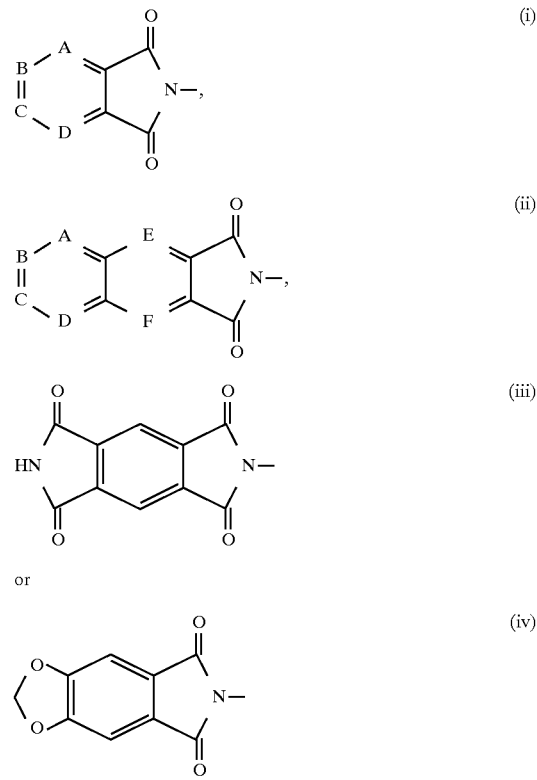

in which A, B, C and D are each CH or 1 or 2 of A, B, C and D represents N and the others represent CH, and E and F each independently represent CH or N and where the optional substituents in formulas (i), (ii), (iii), and (iv) are halogen, hydroxyl, phenyl, $(C_1-C_6)alkyl$, $(C_1-C_6)alkoxy$, or $(C_1-C_6)alkylthio$;

$R^2$ is hydrogen, $(C_1-C_6)alkyl$, $(C_6-C_{10})aryl$, $(C_5-C_9)$heteroaryl, $(C_5-C_9)heteroaryl(C_1-C_6)alkyl$, $(C_6-C_{10})aryl(C_1-C_6)alkyl$, $(C_1-C_6)alkylthio(C_1-C_6)alkyl$, $(C_1-C_6)alkylsulfinyl(C_1-C_6)alkyl$, $(C_1-C_6)alkylsulfonyl(C_1-C_6)alkyl$, $[(C_3-C_6)cycloalkyl](C_1-C_4)alkyl$ or $(C_1-C_6)alkyl$ substituted by a substituent selected from the group consisting of hydroxy, amino, $(C_1-C_6)alkylamino$, $((C_1-C_6)alkyl)_2amino$, $—COOR^4$, and $—CONR^5R^6$, wherein $R^4$, $R^5$ and $R^6$ are each independently selected from the group consisting of hydrogen, $(C_1-C_6)alkyl$, $(C_6-C_{10})aryl(C_1-C_6)alkyl$, and $(C_5-C_9)heteroaryl(C_1-C_6)alkyl$; and, $R^3$ is hydrogen, $(C_6-C_{10})aryl$, $(C_5-C_9)heteroaryl$, $(C_1-C_6)alkyl$, $(C_6-C_{10})aryl(C_1-C_6)alkyl$, $(C_5-C_9)heteroaryl(C_1-C_6)alkyl$, piperidyl$(C_1-C_6)alkyl$, N-$((C_1-C_6)alkyl)piperidyl(C_1-C_6)alkyl$, or $(C_2-C_6)alkyl$ substituted by hydroxy, piperazino, amino, $((C_1-C_6alkyl)amino$, $((C_1-C_6)alkyl)_2amino$, morpholino, thiomorpholino, piperidino, pyrrolidino, N-acylpiperazino, N-$((C_1-C_6)alkyl)piperazino$, N-$((C_6-C_{10})aryl)piperazino$, N-$((C_5-C_9)heteroaryl)piperazino$, N-$((C_6-C_{10})aryl(C_1-C_6)alkyl)piperazino$, N-$((C_5-C_9)heteroaryl(C_1-C_6)alkyl)piperazino$, $(C_1-C_6)alkylthio$, sulfinyl or sulfoxyl.

The term "alkyl", as used herein, unless otherwise indicated, includes saturated monovalent hydrocarbon radicals having straight, branched or cyclic moieties or combinations thereof.

The term "alkoxy", as used herein, includes O-alkyl groups wherein "alkyl" is defined above.

The term "aryl", as used herein, unless otherwise indicated, includes an organic radical derived form an aromatic hydrocarbon by removal of one hydrogen, such as phenyl or naphthyl, optionally substituted by 1 to 3 substituents selected from the group consisting of fluoro, chloro, trifluoromethyl, ($C_1$–$C_6$)alkoxy, ($C_6$–$C_{10}$)aryloxy, trifluoromethoxy, difluoromethoxy and ($C_1$–$C_6$)alkyl.

The term "heteroaryl", as used herein, unless otherwise indicated, includes an organic radical derived from an aromatic heterocyclic compound by removal of one hydrogen, such as pyridyl, furyl, pyrryl, thienyl, isothiazolyl, imidazolyl, benzimidazolyl, tetrazolyl, pyrazinyl, pyrimidyl, quinolyl, isoquinolyl, benzofuryl, isobenzofuryl, benzothienyl, pyrazolyl, indolyl, isoindolyl, purinyl, carbazolyl, isoxazolyl, thiazolyl, oxazolyl, benzthiazolyl or benzoxazolyl, optionally substituted by 1 to 2 substituents selected from the group consisting of fluoro, chloro, trifluoromethyl, ($C_1$–$C_6$)alkoxy, ($C_6$–$C_{10}$)aryloxy, trifluoromethoxy, difluoromethoxy and ($C_1$–$C_6$)alkyl.

The compounds of formula I have chiral centers and therefore exist in different enantiomeric forms. This invention relates to all optical isomers and stereoisomers of the compounds of formula I and mixtures thereof.

Preferred compounds of formula I include those in which Y is $CH_2$.

Other preferred compounds of formula I include those in which X is $CH_2$.

Other preferred compounds of formula I include those in which $R^1$ is 1,3-dioxo-1,3dihydrobenzo[f]isoindolyl.

Other preferred compounds of formula I include those in which $R^3$ is methyl.

Specific preferred compounds having the stereochemistry of formula I for the $R^2$ substituent include the following:

4-(1,3-dioxo-1,3-dihydrobenzo[f]isoindol-2-yl)-2-{1-[2-(4-methoxyphenyl)-1-(methylcarbamoyl)ethylcarbamoyl]cyclohexylmethyl}butyric acid;

4-(1,3-dioxo-5-methoxy-1,3-dihydroisoindol-2-yl)-2-{1-[2-(4-methoxyphenyl)-1-(methylcarbamoyl)ethylcarbamoyl]cyclohexylmethyl}butyric acid;

4-(1,3-dioxo-5-propoxy-1,3-dihydroisoindol-2-yl)-2-{1-[2-(4-methoxyphenyl)-1-(methylcarbamoyl)ethylcarbamoyl]cyclohexylmethyl}butyric acid;

4-(1,3-dioxo-1,3-dihydro-2H-benzo[f]isoindol-2-yl)-2-{1-[1-(methylcarbamoyl)-2-phenylethylcarbamoyl]cyclohexylmethyl}butyric acid;

4-(1,3-dioxo-1,3-dihydro-2H-benzo[f]isoindol-2-yl)-2-{1-[2-(4-methoxypheny)-1-(methylcarbamoyl)ethylcarbamoyl]cyclohexylaminol}butyric acid;

4-(1,3-dioxo-1,3-dihydro-2H-benzo[f]isoindol-2-yl)-2-{1-[2-(4-methoxypheny)-1-(phenylcarbamoyl)ethylcarbamoyl]cyclohexylmethyl}butyric acid;

2-{1-[2,2-dimethyl-1-(methylcarbamoyl)propylcarbamoyl]cyclohexylmethyl}-4-(1,3-dioxo-1,3-dihydro-2H-benzo[f]isoindol-2-yl)butyric acid;

2-{4,4-difluoro-1-[2-(4-methoxyphenyl)-1-(methylcarbamoyl)ethylcarbamoyl]cyclohexylmethyl}-4-(1,3-dioxo-1,3-dihydro-2H-benzo[f]isoindol-2-yl)butyric acid;

2-{1-[2,2-dimethyl-1-(methylcarbamoyl)propylcarbamoyl]cyclohexylamino}-4-(1,3-dioxo-1,3-dihydro-2H-benzo[f]isoindol-2-yl)butyric acid;

4-(5,7-dioxo-5,7-dihydro-[1,3]-dioxolo[4,5-f]isoindol-6-yl)-2-{1-[1-(methylcarbamoyl)-2-phenylethylcarbamoyl]cyclohexylmethyl}butyric acid;

4-(1,3-dioxo-1,3-dihydro-2H-pyrrolo[3,4-b]quinolin-2-yl)-2-{1-[1-(methylcarbamoyl)-2-phenylethylcarbamoyl]cyclohexylmethyl}butyric acid;

4-(5,7-dioxo-5,7-dihydro-[1,3]-dioxolo[4,5-f]isoindol-6-yl)-2-{1-[1-(methylcarbamoyl)-2-phenylethylcarbamoyl]cyclohexylamino}butyric acid; and, 4-(1,3-dioxo-1,3-dihydro-2H-pyrrolo[3,4-b]quinolin-2-yl)-2-{1-[1-(methylcarbamoyl)-2-phenylethylcarbamoyl]cyclohexylamino}butyric acid.

The present invention also relates to a pharmaceutical composition for (a) the treatment of a condition selected from the group consisting of arthritis, cancer, tissue ulceration, restenosis, periodontal disease, epidermolysis bullosa, scleritis and other diseases characterized by matrix metalloproteinase activity, AIDS, sepsis, septic shock and other diseases involving the production of tumor necrosis factor (TNF) or (b) the inhibition of matrix metalloproteinases or the production of tumor necrosis factor (TNF) in a mammal, including a human, comprising an amount of a compound of formula I or a pharmaceutically acceptable salt thereof, effective in such treatments and a pharmaceutically acceptable carrier.

The present invention also relates to a method for the inhibition of (a) matrix metalloproteinases or (b) the production of tumor necrosis factor (TNF) in a mammal, including a human, comprising administering to said mammal an effective amount of a compound of formula I or a pharmaceutically acceptable salt thereof.

The present invention also relates to a method for treating a condition selected from the group consisting of arthritis, cancer, tissue ulceration, restenosis, periodontal disease, epidermolysis bullosa, scleritis and other diseases characterized by matrix metalloproteinase activity, AIDS, sepsis, septic shock and other diseases involving the production of tumor necrosis factor (TNF) in a mammal, including a human, comprising administering to said mammal an effective amount of a compound of formula I or a pharmaceutically acceptable salt thereof.

DETAILED DESCRIPTION OF THE INVENTION

The following reaction Schemes 1 and 2 illustrate the preparation of the compounds of the present invention. Unless otherwise indicated $R^1$, $R^2$, $R^3$, X and Y in the reaction Schemes and the discussion that follow are as defined above.

Scheme 1
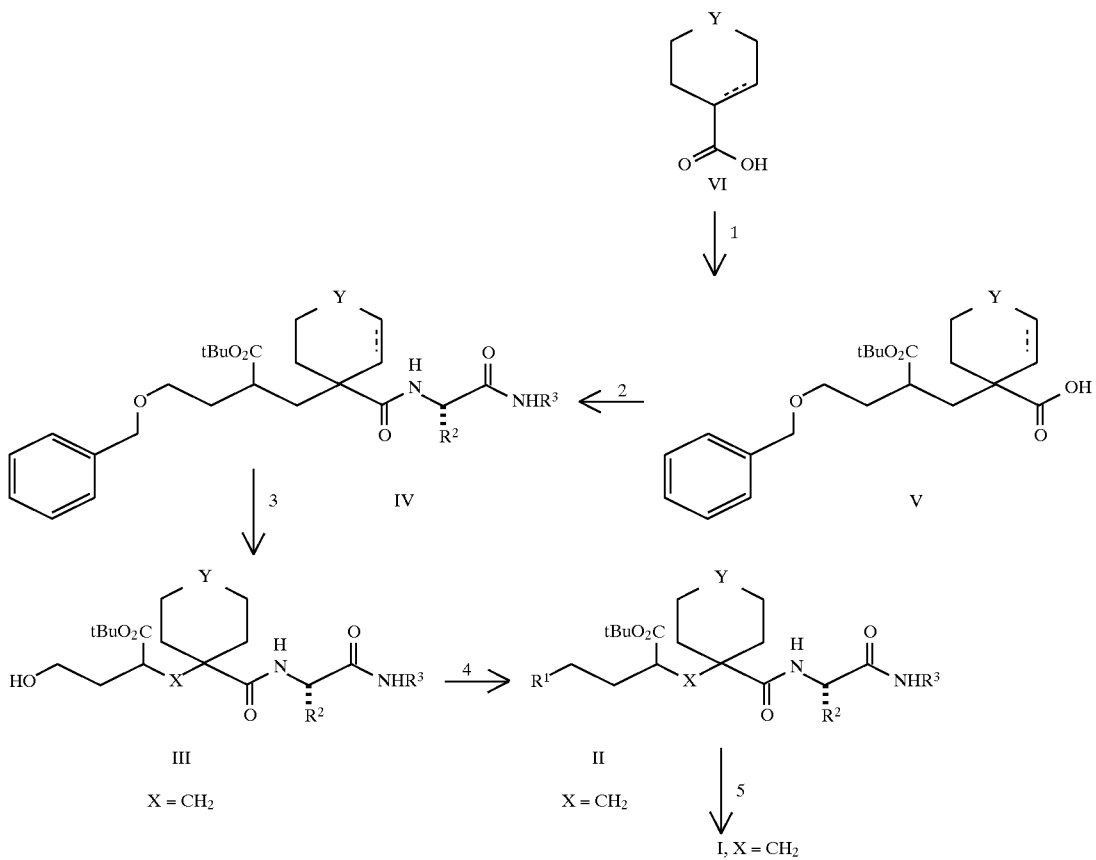
Scheme 2
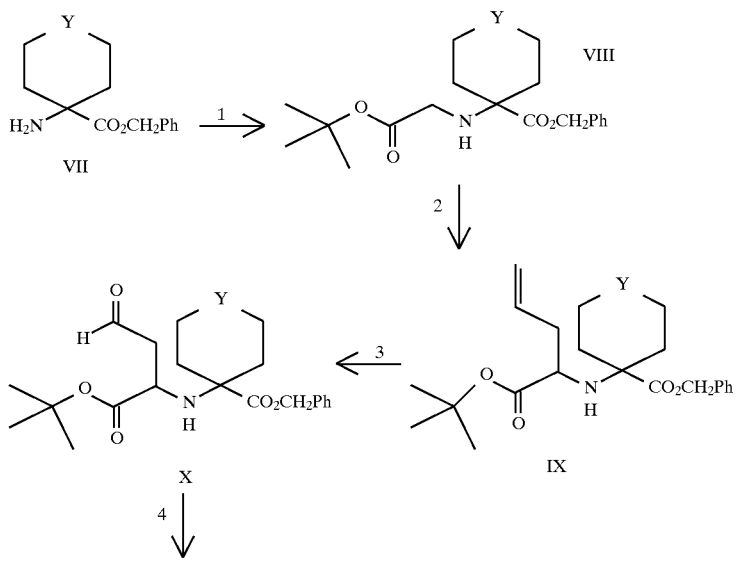

-continued
Scheme 2

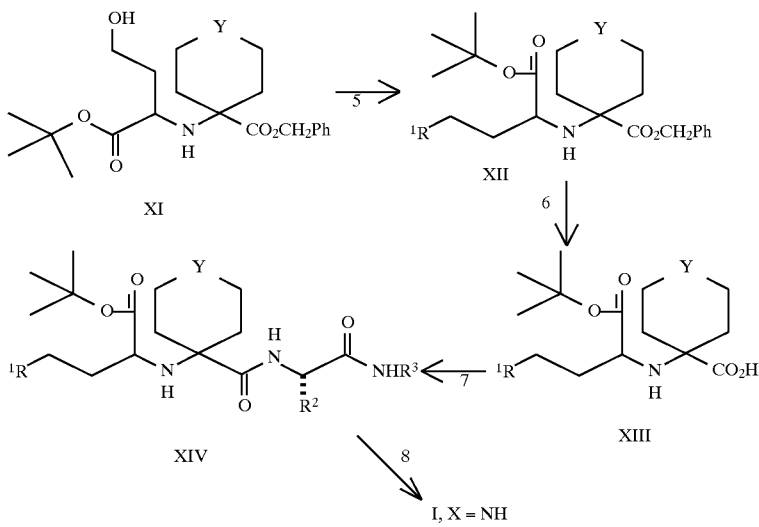

Scheme 1 illustrates the preparation of compounds of formula I wherein X is CH$_2$. In reaction 1 of Scheme 1, the carboxylic acid of formula VI (double C—C bond indicated by dotted line is optional) is reacted with at least two equivalents strong base, such as lithium diisopropylamine, in a polar solvent, such as tetrahydrofuran (preferred) or diethylether, at a temperature of −78° C. to 25° C. over a period of 1 hour to 12 hours (preferably 2 hours). The reaction mixture is then cooled to a temperature of −78° C. to −50° C., and a solution of tert-butyl-2-(2-benzyloxyethyl) acrylate in a polar solvent such as tetrahydrofuran (preferred) or diethylether is added. The resulting reaction mixture is stirred at atemperature of −78° C. to −20° C. for a period of 1 hour to 12 hours (2 hours preferred). After acidic workup and chromatography, the compound of formula V is obtained as a mixture of diastereomers.

In reaction 2 of Scheme 1, the carboxylic acid of formula V is coupled with an L-amino acid derivative of formula VII (or salt thereof:

$$H_2NCH(R^2)CONHR^3 \quad (VII)$$

wherein R2 and R3 are as defined above. In this step, a compound of formula IV is obtained (as a mixture of diastereomers) using a coupling method well known those skilled in the art of peptide chemistry. The preferred coupling method is to combine the compounds of formulas V and VII, 1-hydroxybenztriazole, 1-(3-dimethylaminopropyl) -ethylcarbodiimide hydrochloride and a base, such as triethylamine, in an inert solvent, such as methylene chloride, at a temperature of 0° C. to 30° C. (20°–25° C. preferred) for a period of 2 hours to 48 hours (24 hours preferred).

In reaction 3 of Scheme 1, the compound of formula IV is hydrogenated over 20% palladium hydroxide on carbon in a suitable solvent, such as methanol or ethanol, for a period of 4 hours to 48 hours (24 hours preferred) under 3 atmospheres pressure of hydrogen to obtain an alcohol of formula III wherein X is CH$_2$.

In reaction 4 of Scheme 1, the compound of formula III is reacted with a compound R$^1$H, wherein R$^1$ is a cyclic imido group as defined above, in the presence of an activating system such as triphenylphosphine and diethylazodicarboxylate to obtain a compound of formula II.

In reaction 5 of Scheme 1, the compound of formula I is obtained by treating the compound of formula II with an acid, such as trifluoroacetic acid or hydrochloric acid, to remove the tert-butyl leaving group to give the corresponding carboxylic acid. Reactions analogous to reactions 4 and 5 of Scheme 1 are referred to in European Patent Publication Number 520,573 A1, published Dec. 30, 1992 U.S. Pat. No. 5,252,560, the disclosure of which is herein incorporated by reference.

Compounds of formula I wherein X is NH are prepared by the sequence illustrated in Scheme 2. In reaction 1 of Scheme 2, the compound of formula VII is reacted with one equivalent of tert-butyl bromoacetate in a solvent, such as N,N-dimethylformamide (DMF), with 2.5 equivalents base, such as diisopropylamine, in the presence of about 0.1 equivalents sodium iodide, at a temperature of about 50° C. for about 24 hours to obtain a compound of formula VII. In reaction 2 of Scheme 2, the compound of formula VIII is reacted with 1.5 equivalents of allyl bromide in a polar solvent, such as tetrahydrofuran (preferred) or diethylether, with 1.5 equivalents strong base, such as lithium diisopropylamine, at a temperature ranging from about −78° C. to about 0° C. for about 4 hours to obtain a compound of formula IX.

In reaction 3 of Scheme 2, the compound of formula IX is reacted with 3 equivalents of an oxidizing agent, such as sodium periodate, and a catalytic amount of osmium tetroxide in a solvent, such as dioxane and water, at ambient temperature (22°–25° C.) for about 6 hours to obtain the compound of formula X. In reaction 4 of Scheme 2, the compound of formula X is reacted with 2 equivalents of reducing agent, such as sodium borohydride, in a solvent, such as methanol, at ambient temperature for about 24 hours to obtain the compound of formula XI.

In reaction 5 of Scheme 2, the compound of formula XI is reacted with a compound R$^1$H, wherein R$^1$ is a cyclic imido group as defined above, in the presence of an activating system such as triphenylphosphine and diethylazodicarboxyate to obtain a compound of formula XII. The reaction period for reaction 5 is from 1 to 7 days, with 6 days preferred. In reaction 6 of Scheme 2, the compound of formula XII is hydrogenated (3 atm) over 10% palladium on carbon in a suitable solvent, such as acetic acid, at ambient temperature for about 2 hours to obtain a compound of formula XIII. In reaction 7 of Scheme 2, the compound of formula XIII is coupled with an L-amino acid derivative (or salt thereof) having the formula XV: $H_2NCH(R^2)CONHR^3$, wherein $R^2$ and $R^3$ are as defined above. In this step, a compound of formula XIV is obtained (as a mixture of diastereomers) using a coupling method well known those skilled in the art of peptide chemistry. The preferred coupling method is to combine the compounds of formulas XV and XIII, 1-hydroxybenztriazole, 1-(3-dimethylaminopropyl)-3-ethylcarbodiimide hydrochloride and a base, such as triethylamine, in an inert solvent, such as methylene chloride, at a temperature of 0° C. to 30° C. (20°–25° C. preferred) for a period of 2 hours to 96 hours (72 hours preferred).

In reaction 8 of Scheme 2, the compound of formula I is obtained by treating the compound of formula XIV with an acid, such as trifluoroacetic acid or hydrochloric acid, to remove the tert-butyl leaving group to give the corresponding carboxylic acid. Reactions analogous to reactions 5 and 8 of Scheme 2 are referred to in European Patent Publication Number 520,573 A1, published Dec. 30, 1992 U.S. Pat. No. 5,252,560, the disclosure of which is herein incorporated by reference.

Pharmaceutically acceptable salts of the acidic compounds of the invention are salts formed with bases, namely cationic salts such as alkali and alkaline earth metal salts, such as sodium, lithium, potassium, calcium, magnesium, as well as ammonium salts, such as ammonium, trimethylammonium, diethylammonium, and tris(hydroxymethyl)-methylammonium salts.

Similarly acid addition salts, such as of mineral acids, organic carboxylic and organic sulfonic acids (e.g.hydrochloric acid, methanesulfonic acid, and maleic acid) are also possible provided a basic group, such as pyridyl, constitutes part of the structure.

The ability of the compounds of formula I and their pharmaceutically acceptable salts to inhibit matrix metalloproteinases or the production of tumor necrosis factor (TNF) and, consequently, demonstrate their affectiveness for treating diseases characterized by matrix metalloproteinase or the production of tumor necrosis factor is shown by the following in vitro assay tests.

Biological Assay

Inhibition of Human Collagenase (MMP-1)

Human recombinant collagenase is activated with trypsin using the following ratio: 10 µg of trypsin per 100 µg of collagenase. The trypsin and collagenase are incubated at room temperature for 10 minutes then a five fold excess (50 µg/10 µg trypsin) of soybean trypsin inhibitor is added.

10 mM stock solutions of inhibitors are made up in dimethyl sulfoxide and then diluted using the following Scheme:

10 mM→120µM→12 µM→1.2 µM→0.12 µM

Twenty-five microliters of each concentration is then added in triplicate to appropriate wells of a 96 well microfluor plate. The final concentration of inhibitor will be a 1:4 dilution after addition of enzyme and substrate. Positive controls (enzyme, no inhibitor) are set up on wells D1–D6 and blanks (no inhibitors, no enzyme) are set up on wells D7–D12.

Collagenase is diluted to 400 ng/ml and 25 µl is then added to appropriate wells of the microfluor plate.

Substrate [Dnp-Pro-Cha-Gly-Cys(Me)-His-Ala-Lys(NMA)-$NH_2$] is made up as a 5 mM stock solution in dimethyl sulfoxide and then diluted to 20 µM in assay buffer. The assay is initiated by the addition of 50 µl substrate per well of the microfluor plate to give a final concentration of 10 µM.

Fluorescence readings (360 nM excitation; 460 nM emission) were taken at time 0 and then at 20 minute intervals. The assay is conducted at room temperature with a typical assay time of 3 hours.

Fluorescence vs time is then plotted for both the blank and collagenase containing samples (data from triplicate determinations is averaged). A time point that provides a good signal (the blank) and that is on a linear part of the curve (usually around 120 minutes) is chosen to determine $IC_{50}$ values. The zero time is used as a blank for each compound at each concentration and these values are subtracted from the 120 minute data. Data is plotted as inhibitor concentration vs % control (inhibitor fluorescence divided by fluorescence of collagenase alone×100). $IC_{50}$'s are determined from the concentration of inhibitor that gives a signal that is 50% of the control.

Inhibition of Gelatinase (MMP-2)

Inhibition of gelatinase activity is assayed using the Dnp-Pro-Cha-Gly-Cys(Me)-His-Ala-Lys(NMA)-$NH_2$ substrate (10 µM) under the same conditions as inhibition of human collagenase (MMP-1).

72 kD gelatinase is activated with 1 mM APMA (p-aminophenyl mercuric acetate) for 15 hours at 4° C. and is diluted to give a final concentration in the assay of 100 mg/ml. Inhibitors are diluted as for inhibition of human collagenase (MMP-1) to give final concentrations in the assay of 30 µM, 3 µM, 0.3 µM and 0.03 µM. Each concentration is done in triplicate.

Fluorescence readings (360 nm excitation, 460 emission) are taken at time zero and then at 20 minute intervals for 4 hours.

$IC_{50}$'s are determined as per inhibition of human collagenase (MMP-1). If $IC_{50}$'s are reported to be less than 0.03 µM, then the inhibitors are assayed at final concentrations of 0.3 µM, 0.03 µM, 0.003 µM and 0.0003 µM.

Inhibition of Stromelysin Activity (MMP-3)

Inhibition of stromelysin activity is based on a modified spectrophotometric assay described by Weingarten and Feder (Weingarten, H. and Feder, J., Spectrophotometric Assay for Vertebrate Collagenase, Anal. Biochem. 147, 437–440 (1985)). Hydrolysis of the thio peptolide substrate [Ac-Pro-Leu-Gly-SCH[$CH_2CH(CH_3)_2$]CO-Leu-Gly-$OC_2H_5$] yields a mercaptan fragment that can be monitored in the presence of Ellman's reagent.

Human recombinant prostromelysin is activated with trypsin using a ratio of 1 µl of a 10 mg/ml trypsin stock per 26 µg of stromelysin. The trypsin and stromelysin are incubated at 37° C. for 15 minutes followed by 10 µl of 10 mg/ml soybean trypsin inhibitor for 10 minutes at 37° C. for 10 minutes at 37° C to quench trypsin activity.

Assays are conducted in a total volume of 250 µl of assay buffer (200 mM sodium chloride, 50 mM MES, and 10 mM calcium chloride, pH 6.0) in 96-well microliter plates. Activated stromelysin is diluted in assay buffer to 25 µg/ml. Ellman's reagent (3-Carboxy4-nitrophenyl disulfide) is made as a 1M stock in dimethyl formamide and diluted to 5 mM in assay buffer with 50 µl per well yielding at 1 mM final concentration.

10 mM stock solutions of inhibitors are made in dimethyl sulfoxide and diluted serially in assay buffer such that addition of 50 μL to the appropriate wells yields final concentrations of 3 μM, 0.3 μM, 0.003 μM, and 0.0003 μM. All conditions are completed in triplicate.

A 300 mM dimethyl sulfoxide stock solution of the peptide substrate is diluted to 15 mM in assay buffer and the assay is initiated by addition of 50 μl to each well to give a final concentration of 3 mM substrate. Blanks consist of the peptide substrate and Ellman's reagent without the enzyme. Product formation was monitored at 405 nm with a Molecular Devices UVmax plate reader.

$IC_{50}$ values were determined in the same manner as for collagenase.

Inhibition of MMP-13

Human recombinant MMP-13 is activated with 2 mM APMA (p-aminophenyl mercuric acetate) for 1.5 hours, at 37° C. and is diluted to 400 mg/ml in assay buffer (50 mM Tris, pH 7.5, 200 mM sodium chloride, 5 mM calcium chloride, 20 μM zinc chloride, 0.02% brij). Twenty-five microliters of diluted enzyme is added per well of a 96 well microfluor plate. The enzyme is then diluted in a 1:4 ratio in the assay by the addition of inhibitor and substrate to give a final concentration in the assay of 100 mg/ml.

10 mM stock solutions of inhibitors are made up in dimethyl sulfoxide and then diluted in assay buffer as per the inhibitor dilution scheme for inhibition of human collagenase (MMP-1): Twenty-five microliters of each concentration is added in triplicate to the microfluor plate. The final concentrations in the assay are 30 μM, 3 μM, 0.3 μM, and 0.03 μM.

Substrate (Dnp-Pro-Cha-Gly-Cys(Me)-His-Ala-Lys (NMA)-$NH_2$) is prepared as for inhibition of human collagenase (MMP-1) and 50 μl is added to each well to give a final assay concentration of 10 μM. Fluorescence readings (360 nM excitation; 450 nM emission) are taken at time 0 and every 5 minutes for 1 hour.

Positive controls consist of enzyme and substrate with no inhibitor and blanks consist of substrate only.

$IC_{50}$'s are determined as per inhibition of human collagenase (MMP-1). If $IC_{50}$'s are reported to be less than 0.03 μM, inhibitors are then assayed at final concentrations of 0.3 μM, 0.03 μM, 0.003 μM and 0.0003 μM.

Inhibition of TNF Production

The ability of the compounds or the pharmaceutically acceptable salts thereof to inhibit the production of TNF and, consequently, demonstrate their effectiveness for treating diseases involving the production of TNF is shown by the following in vitro assay:

Human mononuclear cells were isolated from anticoagulated human blood using a one-step Ficoll-hypaque separation technique. The mononuclear cells were washed three times in Hanks balanced salt solution (HBSS) with divalent cations and resuspended to a density of $2 \times 10^6$/ml in HBSS containing 1% BSA. Differential counts determined using the Abbott Cell Dyn 3500 analyzer indicated that monocytes ranged from 17 to 24% of the total cells in these preparations.

180 μl of the cell suspension was aliquoted into flate bottom 96 well plates (Costar). Additions of compounds and LPS (100 ng/ml final concentration) gave a final volume of 200 μl. All conditions were performed in triplicate. After a four hour incubation at 37° C. in an humidified $CO_2$ incubator, plates were removed and centrifuged (10 minutes at approximately 250×g) and the supernatants removed and assayed for TNFα using the R&D ELISA Kit.

For administration to humans for the inhibition of matrix metalloproteinases or the production of tumor necrosis factor (TNF), any conventional administration method may be used including oral, parenteral and topical methods of administration. In general, the active compound will be administered orally or parenterally at dosages between about 0.1 and 25 mg/kg body weight of the subject to be treated per day, preferably from about 0.3 to 5 mg/kg. However, some variation in dosage will necessarily occur depending on the condition of the subject being treated. The person responsible for administration ultimately will determine the appropriate dose for the individual subject.

The compounds of the present invention can be administered in a wide variety of different dosage forms. In general, the therapeutically effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (preferably corn, potato or tapioca starch), alginic acid and certain complex silicates, together with granulation binders like polyvinylpyrrolidone, sucrose, gelation and acacia. Additionally, lubricating agents such as magnesium stearate, sodium lauryl sulfate and talc are often very useful for tabletting purposes. Solid compositions of a similar type may also be employed as fillers in gelatin capsules. Preferred filling materials include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if desired, emulsifying and/or suspending agents as well, together with such diluents as water, ethanol, propylene glycol, glycerin and various like combinations thereof.

For parenteral administration (including intramuscular, intraperitoneal, subcutaneous and intravenous administration) a sterile injectable solution of the active ingredient is usually prepared. Solutions of a compound of formula I in either sesame or peanut oil or in aqueous propylene glycol may be employed. The aqueous solutions should be suitably adjusted and buffered, preferably at a pH of greater than 8, and the liquid diluent first rendered isotonic. These aqueous solutions are suitable for intravenous administration. The oily solutions are suitable for intraarticular, intramuscular and subcutaneous administration. The preparation of the foregoing aqueous and oily solutions under sterile conditions is readily accomplished by standard pharmaceutical techniques familiar to those skilled in the art.

The present invention is illustrated by the following examples, but it is not limited to the details thereof. Certain compounds are described as "diastereomer A" or "diastereomer B". The absolute or relative chemistry of these compounds has not been determined but the nomenclature used is intended to represent that A and B compounds are diastereomers of each other. It is believed that the diastereomerism stems from the chiral carbon-2 of the butyric acid described as diastereomer A or B.

EXAMPLE 1

4-(1,3-dioxo-1,3-dihydrobenzo[f]isoindol-2-yl)-2-{1-[2-(4-methoxyphenyl)-1-(methylcarbamoyl) ethylcarbamoyl] cyclohexylmethyl}butyric acid (diastereomer A)

A. To an ice-cooled mechanically stirred solution of 2-benzyloxyethanol (25 mL, 0.18 mole), triphenylphosphine (115.2 g, 0.44 mole) and pyridine (56.9 mL, 0.70 mole) in methylene chloride (1000 mL) was added, dropwise, carbon tetrabromide (61.3 g, 0.18 mole). The mixture was stirred overnight at room temperature. Methanol (130 mL) was then added and, after further stirring for 1 hour, the solvents were evaporated. The residue was triturated with hexane and the hexane solution was concentrated to yield an oil which was set aside. The residue remaining after trituration was taken up in ethyl acetate, washed with saturated sodium bicarbonate solution and brine and was concentrated to afford a brown oil. This was triturated with hexane. The resulting hexane solution was combined with the oil from the previous trituration and concentrated. The residue was chromatographed twice on silica gel eluting with hexane and then 5% ethyl acetate/hexane to afford (2-bromoethoxymethyl) benzene as an oil (28.8 g, 76% yield).

B. To a suspension of sodium hydride (3.22 g, 0.134 mole) in N,N-dimethylformamide (DMF)(150 mL) was added tert-butyl ethyl malonate (22.9 g, 0.122 mole). The resulting mixture was stirred at room temperature for 1 hour and then a solution of (2-bromoethoxymethyl)benzene (28.8 g, 0.134 mole) in DMF (150 mL) was added dropwise. After stirring at room temperature overnight, the mixture was poured into water (1000 mL) and extracted with ethyl acetate. The ethyl acetate layer was washed with water and brine, dried over magnesium sulfate and concentrated to an oil which was chromatographed on silica gel eluting with hexane and then 5% ethyl acetate in hexane to afford 2-(2-benzyloxyethyl)malonic acid tert-butyl ester ethyl ester as an oil (31.4 g, 80% yield).

C. To a solution of 2-(2-benzyloxyethyl) malonic acid tert-butyl ester ethyl ester (31.3 g, 97.1 mmol) in water (50 mL) and dioxane (200 mL) was added potassium hydroxide (6.6 g, 0.118 mole) while cooling in an ice bath. The mixture was then stirred at room temperature overnight. The solvents were evaporated under vacuum to leave a clear oil which was dissolved in water. The solution was washed with ether and then acidified to pH 3 using 6N hydrogen chloride (HCl) solution. The mixture was extracted twice with ether; the extracts were combined, washed with brine, dried over magnesium sulfate ($MgSO_4$) and concentrated under vacuum to leave 2-(2-benzyloxyethyl) malonic acid mono tert-butyl ester as a clear oil, 23.9 g (84%).

D. A solution of 2-(2-benzyloxyethyl) malonic acid mono tert-butyl ester (23.9 g, 81.2 mmol), piperidine (1.31 mL, 13.2 mmol), and paraformaldehyde (3.7 g, 123 mmol) in pyridine (160 mL) was heated at a temperature of 70° C. for 3 hours. After cooling to room temperature, the mixture was poured over ice. The mixture was acidified using 6N HCl solution and then extracted twice with ether; the extracts were combined, washed with brine, dried over $MgSO_4$ and concentrated under vacuum to leave an oil. The oil was chromatographed on silica gel using 6% ethyl acetate in hexane to afford 2-(2-benzyloxyethyl)acrylic acid tert-butyl ester as a clear oil, 18.51 g (87%).

E. To a solution of diisopropylamine (8.8 mL, 62.8 mmol) in dry tetrahydrofuran (140 mL) at −50° C. was added a 2.5M solution of n-butyllithium in hexane (25 mL, 12.5 mmol). The mixture was stirred at a temperature from −50° C. to −20° C. over 30 minutes and then cooled again to −50° C. Solid 1-cyclohexene carboxylic acid (3.75 g, 29.7 mmol) was added and the resulting mixture was allowed to warm to room temperature with stirring over 1.5 hours. The reaction was cooled to −78° C. and a solution of 2-(2-benzyloxyethyl)acrylic acid tert-butyl ester (7.45 g, 28.4 mmol) in dry tetrahydrofuran (90 mL) was added over 15 minutes; stirring was continued at −78° C. for 5 hours. The mixture was then allowed to warm to −30° C. over 40 minutes and was quenched by the addition of saturated aqueous $NH_4Cl$ solution. After acidification using 3N HCl solution, the mixture was extracted with ether. The extract was washed with brine, dried over $MgSO_4$ and evaporated under vacuum to leave a yellow oil from which 1-(4-benzyloxy-2-tert-butoxycarbonylbutyl)cyclohex-2-ene carboxylic acid (an oily mixture of the two diastereomers), 9.71 g (84%) was isolated by chromatography on silica gel eluting with methylene chloride and then 5% methanol in methylene chloride.

F. To a solution of 1-(4-benzyloxy-2-tert-butoxycarbonylbutyl) cyclohex-2-ene carboxylic acid (a mixture of the two diastereomers) (2.5 g, 6.43 mmol) in methylene chloride (100 mL) were added successively L-tyrosine methyl ether N-methylamide hydrochloride (1.7 g, 6.95 mmol), 1-hydroxybenztriazole hydrate (959 mg, 6.26 mmol), triethylamine (0.98, 7.03 mmol) and 1-(3-dimethylaminopropyl)-3-ethylcarbodimide hydrochloride (1.36 g, 7.09 mmol). The resulting mixture was stirred overnight at room temperature and, after dilution with methylene chloride, was washed with 0.5M HCl solution and brine. The solvent was removed by evaporation under reduced vacuum leaving an oil which was chromatographed on silica gel eluting with 50% ethyl acetate in hexane. Fractions enriched in the desired product (4-benzyloxy-2-{1-[2-(4-methoxy-phenyl)-1-(methylcarbamoyl) ethylcarbamoyl]cyclohex-2-enylmethyl}butyric acid tert-butyl ester) were combined and concentrated to leave an oil, 2.2 g. The oil was dissolved in ethanol (50 mL) to which was added 20% palladium hydroxide on carbon (500 mg). The mixture was agitated overnight in a Parr shaker under 3 atmospheres of hydrogen. After removal of the catalyst by filtration through diatomaceous earth, the solvent was evaporated to leave an oil from which 4-hydroxy-2-{1-[2-(4-methoxyphenyl)-1-(methylcarbamoyl)ethylcarbamoyl] cyclohexylmethyl}butyric acid tert-butyl ester, an oily 2:1 mixture of two diastereomers, 1.2 g (38%), was isolated by chromatography on silica gel eluting with 20% hexane in ethyl acetate.

G. To a solution of 4-hydroxy-2-{1-[2-(4-methoxyphenyl)-1-(methylcarbamoyl)-ethylcarbamoyl] cyclohexylmethyl}butyric acid tert-butyl ester (490 mg, 1.0 mmol) in dry tetrahydrofuran (20 mL) was added 1,3-dioxo-1,3-dihydrobenzo[f]isoindole (394 mg, 2.0 mmol), triphenylphosphine (524 mg, 2.0 mmol) and diethylazodicarboxylate (0.31 mL, 2.0 mmol). The resulting mixture was stirred for 3 days. The solvent was evaporated under vacuum and the residue was chromatographed on silica gel eluting with 40% ethyl acetate in hexane. Fractions containing the two diastereomeric products were combined and evaporated to leave a white solid which was recrystallized from ethyl acetate to afford 4-(1,3-dioxo-1,3-dihydrobenzo [f]isoindol-2-yl)-2-{1-[2-(4-methoxyphenyl)-1-(methylcarbamoyl)-ethylcarbamoyl]cyclohexylmethyl}butyric acid tert-butyl ester (diastereomer A) as a white solid, 105 mg (16%). The mother liquor from the recrystallization was concentrated under vacuum to afford an oil highly enriched in diastereomer B, 140 mg (21%).

H. A solution of 4-(1,3-dioxo-1,3-dihydrobenzo[f] isoindol-2-yl)-2-{1-[2-(4-methoxyphenyl)-1-(methylcarbamoyl)ethylcarbamoyl] cyclohexylmethyl}butyricacidtert-butyl ester (diastereomer A) (50 mg, 0.075 mmol) in trifluoroacetic acid (1 mL) was stirred overnight at room temperature. The solvent was evaporated under vacuum leaving a white foam which was titrated with ether to afford 4-(1,3-dioxo-1,3-dihydrobenzo

[f]isoindol-2-yl)-2-{1-[2-(4-methoxyphenyl)-1-(methylcarbamoyl) ethylcarbamoyl]-cyclohexylmethyl}butyric acid (diastereomer A) as a white solid, 40 mg (87%). High Resolution Mass Spectrum M+ calculated for $C_{35}H_{39}N_3O_7$: 613.2788; found: 613.2746.

The following compounds described in Examples 2–6 were prepared similarly to Example 1H:

EXAMPLE 2

4(1,3-Dioxo-1,3-dihydrobenzo[f]isoindol-2-yl)-2-{1-[2-(4-methoxyphenyl)-1-(methylcarbamoyl)ethylcarbamoyl] cyclohexylmethyl}butyric acid 4-(1,3-Dioxo-1,3-dihydrobenzo[f]isoindol-2-yl)-2-{1-[2-(4-methoxyphenyl)-1-(methylcarbamoyl)ethylcarbamoyl] cyclohexylmethyl}butyric acid (diastereomer B); High Resolution Mass Spectrum M+ calculated for $C_{35}H_{39}N_3O_7$: 613.2788; found: 613.2807.

EXAMPLE 3

4-(1,3-Dioxo-1,3-dihydroisoindol-2-yl)-2-{1-[2-(4-methoxyphenyl)-1-(methylcarbamoyl)ethylcarbamoyl] cyclohexylmethyl}butyric acid 4-(1,3-Dioxo-1,3-dihydroisoindol-2-yl)-2-{1-[2-(4-methoxyphenyl)-1-(methylcarbamoyl)ethylcarbamoyl] cyclohexylmethyl}butyric acid (mixture of diastereomers) starting with the reaction of 4-hydroxy-2-{1-[2-(4-methoxyphenyl)-1-(methylcarbamoyl)ethylcarbamoyl] cyclohexylmethyl}butyric acid tert-butyl ester with 1,3-dioxo-1,3-dihydroisoindole.

EXAMPLE 4

4-(1,3-Dioxo-5-methoxy-1,3-dihydroisoindol-2-yl)-2-{1-[2-(4-methoxy-phenyl)-1-(methylcarbamoyl) ethylcarbamoyl]cyclohexylmethyl}butyric acid 4-(1,3-Dioxo-5-methoxy-1,3-dihydroisoindol-2-yl)-2-{1-[2-(4-methoxy-phenyl)-1-(methylcarbamoyl) ethylcarbamoyl]cyclohexylmethyl}butyric acid (mixture of diastereomers) starting with the reaction of 4-hydroxy-2-{1-[2-(4-methoxyphenyl)-1-(methylcarbamoyl) ethylcarbamoyl]cyclohexylmethyl}butyric acid tert-butyl ester with 1,3-dioxo-5-methoxy-1,3dihydroisoindole.

EXAMPLE 5

4-(1,3-Dioxo-5-propoxy-1,3-dihydroisoindol-2-yl)-2-{1-[2-(4-methoxy-phenyl)-1-(methylcarbamoyl)ethylcarbamoyl] cyclohexylmethyl}butyric acid 4-(1,3-Dioxo-5-propoxy-1,3-dihydroisoindol-2-yl)-2-{1-[2-(4-methoxy-phenyl)-1-(methylcarbamoyl) ethylcarbamoyl]cyclohexylmethyl}butyric acid (mixture of diastereomers) starting with the reaction of 4-hydroxy-2-{1-[2-(4-methoxyphenyl)-1-(methylcarbamoyl) ethylcarbamoyl]cyclohexylmethyl}butyric acid tert-butyl ester with 1,3-dioxo-5-propoxy-1,3-dihydroisoindole.

EXAMPLE 6

4-(1,3-Dioxo-1,3-dihydrobenzo[f]isoindol-2-yl)-2-{1-[1-(methylcarbamoyl)-ethylcarbamoyl] cyclohexylmethyl}butyric acid 4-(1,3-Dioxo-1,3-dihydrobenzo[f]isoindol-2-yl)-2-{1-[1-(methylcarbamoyl)-ethylcarbamoyl] cyclohexylmethyl}butyric acid (mixture of diastereomers) starting with the reaction of 1-(4-benzyloxy-2-tert-butoxycarbonylbutyl)cyclohex-2-enecarboxylic acid (a mixture of the two diastereomers) with L-alanine N-methylamide.

EXAMPLE 7

4-(1,3-dioxo-1,3-dihydrobenzo[f]isoindol-2-yl)-2-{1-[2-(4-methoxyphenyl)-1-(methylcarbamoyl)ethylcarbamoyl]-cyclopentylmethyl}butyric acid (diastereomer A)

A. To a solution of diisopropylamine (2.9 mL, 20.8 mmol) in dry tetrahydrofuran (50 mL) at −50° C. was added a 2.5M solution of n-butyllithium in hexane (8.4 mL, 21 mmol). The mixture was stirred at a temperature from −30° C. to 0° C. over 30 minutes and then cooled again to −40° C. A solution of cyclopentanecarboxylic acid (1.1 mL, 10.1 mmol) in tetrahydrofuran (20 mL) was added and the resulting mixture was allowed to warm to room temperature with stirring over 2 hours. The reaction was cooled to −79° C. and a solution of 2-(2-benzyloxyethyl) acrylic acid tert-butyl ester (2.6 g, 9.9 mmol) in dry tetrahydrofuran (10 mL) was added dropwise; stirring was continued at −40° C. for 2 hours. The mixture was quenched by the addition of 0.5M HCl solution and was extracted with ether. The extract was washed with brine, dried over $MgSO_4$ and evaporated under vacuum to leave an oil from which 1-(4-benzyloxy-2-tert-butoxycarbonylbutyl)cyclopentane carboxylic acid, 2.9 g (78%), was isolated by chromatography on silica gel eluting with methylene chloride and then 1% methanol in methylene chloride.

B. To a solution of 1-(4-benzyloxy-2-tert-butoxycarbonylbutyl) cyclocyclopentane-carboxylic acid (2.9 g, 7.7 mmol) in methylene chloride (100 mL) were added successively L-tyrosine methyl ether N-methyl amide hydrochloride (2.1 g, 8.6 mmol), 1-hydroxybenztriazole hydrate (1.1 g, 7.2 mmol), triethylamine (1.2 mL, 8.6 mmol) and 1-(3-dimethylaminopropyl)-3-ethylcarbodiimide hydrochloride (1.6 g, 8.3 mmol). The resulting mixture was stirred overnight at room temperature and, after dilution with methylene chloride, was washed with 0.5M HCl solution and brine. The solvent was removed by evaporation under reduced vacuum leaving an oil from which 4-benzyloxy-2-{1-[2-(4-methoxyphenyl)-1 -(methylcarbamoyl) ethylcarbamoyl]cyclopentylmethyl}-butyric acid tert-butyl ester (an oily mixture of the two diastereomers) was isolated by chromatography on silica gel eluting with 40% ethyl acetate in hexane.

C. 4-Benzyloxy-2-{1-[2-(4-methoxyphenyl)-1-(methylcarbamoyl)ethylcarbamoyl]-cyclopentylmethyl}butyric acid tert-butyl ester (a mixture of the two diastereomers) (1.7 g, 3.0 mmol) was dissolved in ethanol (30 mL) to which was added 20% palladium hydroxide on carbon (300 mg). The mixture was agitated for 4 hours in a Parr shaker under 3 atmospheres of hydrogen. After removal of the catalyst by filtration through diatomaceous earth, the solvent was evaporated to leave 4-hydroxy-2-{1-[2-(4-methoxy-phenyl)-1-(methylcarbarmoyl) ethylcarbamoyl]cyclopentylmethyl}butyric acid tert-butyl ester as an oily mixture of two diastereomers, 1.3 g (91%).

D. To a solution of 4-hydroxy-2-{1-[2-(4-methoxyphenyl)-1-(methylcarbamoyl)ethylcarbamoyl] cyclopentylmethyl}butyric acid tert-butyl ester (500 mg, 1.05 mmol) in dry tetrahydrofuran (20 mL) was added 1,3-dioxo-1,3-dihydrobenzo[f]isoindole (414 mg, 2.1 mmol), triphenylphosphine (550 mg, 2.1 mmol) and diethylazodicarboxylate (0.33 mL, 2.1 mmol) and the resulting mixture was stirred for 10 days. The solvent was evaporated under vacuum and the residue was chromatographed on silica gel eluting with 30% ethyl acetate in hexane. Fractions containing the two diastereomeric products were combined and evaporated to leave a solid which was recrystallized from ethyl acetate to afford 4-(1,3-dioxo-1,3-dihydrobenzo [f]isoindol-2-yl)-2-{1-[2-(4-methoxyphenyl)-1-(methylcarbamoyl)ethylcarbamoyl] cyclopentylmethyl}butyric acid tert-butyl ester (diastereomer A) as a white solid, 45 mg (7%). The mother liquor from the recrystallization was concentrated under vacuum to afford an oil which was taken up in 25% ethyl acetate in hexane and allowed to stand overnight. A small amount of solid was removed by filtration and the solvent was evaporated to give an oil highly enriched in diastereomer B, 60 mg (9%).

E. A solution of 4-(1,3-dioxo-1,3-dihydrobenzo[f] isoindol-2-yl)-2-{1-[2-(4-methoxyphenyl)-1-(methylcarbamoyl)ethylcarbamoyl] cyclopentylmethyl}butyric acid tert-butyl ester (diastereomer A) (45 mg, 0.069 mmol) in trifluoracetic acid (1 mL) was stirred overnight at room temperature. The solvent was evaporated under vacuum leaving a white foam which was triturated with ether to afford 4-(1,3-dioxo-1,3-dihydrobenzo[f]isoindol-2-yl)-2-{1-[2-(4-methoxyphenyl)-1-(methylcarbamoyl)ethylcarbamoyl]-cyclopentylmethyl}butyric acid (diastereomer A) as a white solid, 33 mg (80%). High Resolution Mass Spectrum M+ calculated for $C_{34}H_{37}N_3O_7$: 599.2632; found:

EXAMPLE 8

4-(1,3-Dioxo-1,3-dihydrobenzo[f]isoindol-2-yl)-2-{1-[2-(4-methoxy-phenyl)-1-(methylcarbamoyl)ethylcarbamoyl] cyclopentylmethyl}butyric acid (diastereomer B)

4-(1,3-Dioxo-1,3-dihydrobenzo[f]isoindol-2-yl)-2-{1-[2-(4-methoxy-phenyl)-1-(methylcarbamoyl)ethylcarbamoyl] cyclopentylmethyl}butyric acid (diastereomer B) was prepared similarly to Example 3E. High Resolution Mass Spectrum M+ calculated for $C_{34}H_{37}N_3O_7$: 599.2632; found:

EXAMPLE 9

4-(1,3-dioxo-1,3-dihydrobenzo[f]isoindol-2-yl)-2-{1-[2-(4-methoxyphenyl)-1-(methylcarbamoyl)ethylcarbamoyl] cyclohexyl-amino}butyric acid (trifluoroacetic acid salt)

To a solution of benzyl 1-aminocyclohexanecarboxylate, 4-methylsulfonic acid salt (10.0 g, 25.7 mmol) in dry N,N-dimethylformamide (120 mL) was added sodium iodide (0.37 g, 2.47 mmol) and tert-butyl bromoacetate (3.64 mL, 24.7 mmol). The resulting mixture was stirred at 50° C. for about 24 hours. Most of the N,N-dimethylformamide was removed by evaporation under vacuum. To the residue was added saturated sodium bicarbonate solution and water. The mixture was extracted twice with diethyl ether and the combined organic extracts were washed with brine and dried over magnesium sulfate. The residue obtained upon evaporation of the diethyl ether was chromatographed on silica gel eluting with 5% ethyl acetate in hexane to afford 1-(tert-butoxycarbonylmethylamino)cyclohexanecarboxylic acid benzyl ester as a clear oil, 8.59 g.

To a solution of diisopropylamine (3.03 mL, 21.6 mmol) in dry tetrahydrofuran (75 mL) at −78° C. was added a 2.38M solution of n-butyllithium in hexane (9.07 mL, 21.6 mmol). After 10 minutes, a solution of 1-(tert-butoxycarbonylmethylamino)cyclohexanecarboxylic acid benzyl ester (5.0 g, 14.4 mmol) in tetrahydrofuran (25 mL) was added and the resulting mixture was allowed to warm to −40° C. over 2.5 hours. The mixture was again cooled to −78° C. and allyl bromide was added. The mixture was allowed to warm to 0° C. over 4 hours while stirring and was quenched by addition of a saturated aqueous solution of ammonium chloride. Water was added and the mixture was extracted with ethyl acetate. The organic phase was washed with brine, dried over magnesium sulfate and evaporated under vacuum to afford an oil. The oil was chromatographed on silica gel eluting with 1% ethyl acetate in methylene chloride to give 1-(1-tert-butoxycarbonylbut-3-enylamino)cyclohexanecarboxylic acid benzyl ester as an oil, 2.0 g (36%).

To a solution of (1-tert-butoxycarbonylbut-3-enylamino)-cyclohexanecarboxylic acid (0.5 g, 1.29 mmol) in dioxane (5 mL) and water (5 mL) was added a 2.5 weight % solution of osmium tetroxide in tert-butanol (0.05 mL). After 20 minutes, sodium periodate (0.88 g, 4.13 mmol) was added in small portions over another period of 20 minutes. The mixture was stirred at room temperature for 6 hours and was quenched by addition of a saturated aqueous solution of sodium bicarbonate. The mixture was extracted with ethyl acetate and the extract was washed with brine, dried over magnesium sulfate, and concentrated under vacuum to give an oil. The oil was dissolved in methanol (12 mL) and sodium borohydride (137 mg, 3.61 mmol) was added. The mixture was stirred overnight. A 1M aqueous solution of hydrochloric acid was added and, after stirring for 10 minutes, the solvent was removed under vacuum. The residue was partitioned between a saturated aqueous solution of sodium bicarbonate and ethyl acetate. The organic layer was washed with brine dried over magnesium sulfate, and concentrated under vacuum to give an oil. The oil was chromatographed on silica gel eluting with 10% ethyl acetate in methylene chloride to provide 1-(1-tert-butoxycarbonyl-3-hydroxy-propylamino)cyclohexanecarboxylic acid benzyl ester as an oil, 469 mg (66%).

To a solution of benzyl 1-(1-tert-butoxycarbonyl-3-hydroxy-1-propylamino)cyclohexanecarboxylate (466 mg, 1.19 mmol) in dry tetrahydrofuran (12 mL) was added 1,3-dioxo-1,3-dihydrobenzo[f]isoindole (258 mg, 1.31 mmol), triphenylphosphine (344 mg, 1.31 mmol) and diethylazodicarboxylate (0.21 mL, 1.31 mmol). The resulting mixture was stirred at room temperature for 6 days. The solvent was evaporated under vacuum and the residue was chromatographed on silica gel eluting first methylene chloride and then with 2% ethyl acetate in methylene chloride to afford 1-[1-tert-butoxycarbonyl-3-(1,3-dioxo-1,3-dihydrobenzo[f]isoindol-2-yl)propylamino]cyclohexanecarboxylic acid benzyl ester as a white solid, 530 mg (78%).

1-[1-tert-Butoxycarbonyl-3-(1,3-dioxo-1,3-dihydrobenzo[f]isoindol-2-yl)propylamino]cyclohexanecarboxylic acid benzyl ester (416 mg, 0.729 mmol) was dissolved in acetic acid (85 mL) and 10% palladium on activated carbon (440 mg) was added. The mixture was hydrogenated under 3 atmospheres pressure at room temperature for 2 hours. The catalyst was removed by passage through a 0.45 m nylon filter and the filtrate was concentrated under vacuum to afford 1-[1 -tert-butoxycarbonyl-3-(1,3-dioxo-1,3-dihydrobenzo[f]isoindol-2-yl)propylamino]cyclohexanecarboxylic acid as a white solid, 308 mg (88%).

To a solution of 1-[1-tert-butoxycarbonyl-3-(1,3-dioxo-1,3-dihydrobenzo[f]isoindol-2-yl)propylamino] cyclohexanecarboxylic acid (298 mg,0.62 mmol) in methylene chloride (10 mL) were added successively L-tyrosine methyl ether N-methylamide hydrochloride (180 mg, 0.74 mmol), 1-hydroxybenztriazole hydrate (95 mg, 0.62 mmol), triethylamine (0.12 mL, 0.86 mmol) and 1-(3-dimethylaminopropyl)-3-ethylcarbodiimide hydrochloride (142 mg, 0.74 mmol). The resulting mixture was stirred for 3 days at room temperature. After dilution with methylene chloride, the mixture was washed successively with saturated aqueous sodium bicarbonate, water, 0.5M aqueous hydrochloric acid and brine. The solution was dried over magnesium sulfate. The solvent was removed by evaporation under vacuum leaving an oil which was chromatographed on silica gel eluting with 45% hexane in ethyl acetate to afford 4-(1,3-dioxo-1,3dihydrobenzo[f]isoindol-2-yl)-2-{1-[2-(4-methoxyphenyl)-1 -(methylcarbamoyl)-ethylcarbamoyl]cyclohexylamino}butyric acid tert-butyl ester, diastereomer A (91 mg, 22%) and diastereomer B (85 mg, 20%), in addition to a mixture of diastereomers A and B (169 mg, 41%).

A solution of 4-(1,3-dioxo-1,3-dihydrobenzo[f]isoindol-2-yl)-2-{1-[2-(4-methoxyphenyl)-1-(methylcarbamoyl)ethylcarbamoyl]cyclohexyl-amino}butyricacid<u>tert</u>-butyl ester, diastereomer A (55 mg, 0.082 mmol) in trifluoroacetic acid (2.5 mL) was stirred from 0° C. to room temperature over 24 hours. The solvent was removed under vacuum. Methylene chloride was added and then evaporated under vacuum. The solid residue was triturated with diethyl ether to afford 4-(1,3-dioxo-1,3-dihydrobenzo[f]isoindol-2-yl)-2-{1-[2-(4-methoxyphenyl)-1-(methylcarbamoyl)ethylcarbamoyl]cyclohexyl-amino}butyricacid, trifluoroaceticacidsalt (diastereomer A) as a white solid, 38 mg (64%). [$^1$H NMR (DMSO-d$_6$): δ 8.51 (s, 2 H), 8.29–8.25 (m, 2 H), 7.91–7.89 (m, 1 H), 7.80–7.70 (m, 3 H), 7.09 (d, J=8.5 Hz, 2 H), 6.80 (d, J=8.5 Hz, 2 H), 4.50–4.40 (m, 1 H), 3.67 (s, 3 H). MS: m/z 615 (M+H)]

The same procedure afforded diasteromer B (23 mg, 60%) from the corresponding <u>tert</u>-butyl ester (35 mg, 0.052 mmol). [$^1$H NMR (DMSO-d$_6$): δ 8.50 (s, 2 H), 8.28–8.25 (m, 2 H), 7.80–7.71 (m, 4 H), 7.09 (d, J=8.5 Hz, 2 H), 6.77 (d, J=8.5 Hz, 2 H), 4.47–4.38 (m, 1 H), 3.64 (s, 3 H). MS: m/z 615 (M+H)]

I claim:

1. A compound of the formula

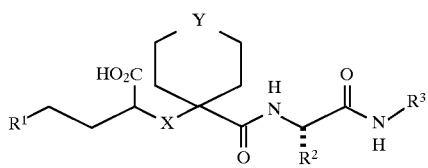

wherein

X is CH$_2$ or NH;

Y is a bond, CH$_2$, CH((C$_1$–C$_6$)alkyl), CF$_2$, S, or O;

R$^1$ is an optionally substituted cyclic imide wherein the cyclic imide ring system has the formula

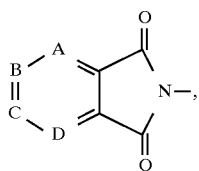

(i)

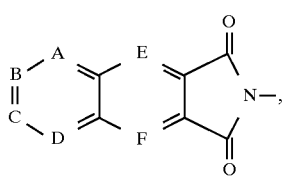

(ii)

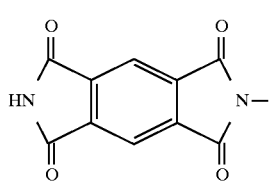

(iii)

or

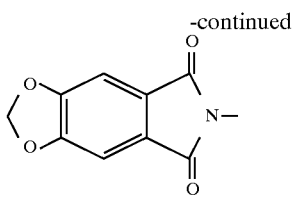

(iv)

in which A, B, C and D are each CH, and E and F each independently represent CH and where the optional substituents in formulas (i), (ii), (iii), and (iv) are halogen, hydroxyl, phenyl, (C$_1$–C$_6$)alkyl, (C$_1$–C$_6$)alkoxy, or (C$_1$–C$_6$)alkylthio;

R$^2$ is hydrogen, (C$_1$–C$_6$)alkyl, (C$_6$–C$_{10}$)aryl, (C$_5$–C$_9$)heteroaryl, (C$_5$–C$_9$)heteroaryl(C$_1$–C$_6$)alkyl, (C$_6$–C$_{10}$)aryl(C$_1$–C$_6$)alkyl, (C$_1$–C$_6$)alkylthio(C$_1$–C$_6$)alkyl, (C$_1$–C$_6$)alkylsulfinyl(C$_1$–C$_6$)alkyl, (C$_1$–C$_6$)alkylsulfonyl(C$_1$–C$_6$)alkyl, [(C$_3$–C$_6$)cycloalkyl](C$_1$–C$_4$)alkyl or (C$_1$–C$_6$)alkyl substituted by a substituent selected from the group consisting of hydroxy, amino, (C$_1$–C$_6$)alkylamino, ((C$_1$–C$_6$)alkyl)$_2$amino, —COOR$^4$, and —CONR$^5$R$^6$, wherein R$^4$, R$^5$ and R$^6$ are each independently selected from the group consisting of hydrogen, (C$_1$–C$_6$)alkyl, (C$_6$–C$_{10}$)aryl(C$_1$–C$_6$)alkyl, and (C$_5$–C$_9$)heteroaryl(C$_1$–C$_6$)alkyl; and, R$^3$ is hydrogen, (C$_6$–C$_{10}$)aryl, (C$_5$–C$_9$)heteroaryl, (C$_1$–C$_6$)alkyl, (C$_6$–C$_{10}$)aryl(C$_1$–C$_6$)alkyl, (C$_5$–C$_9$)heteroaryl(C$_1$–C$_6$)alkyl,piperidyl(C$_1$–C$_6$)alkyl,N-((C$_1$–C$_6$)alkyl)piperidyl(C$_1$–C$_6$)alkyl, or (C$_2$–C$_6$)alkyl substituted by hydroxy, piperazino, amino, ((C$_1$–C$_6$)alkyl)amino, ((C$_1$–C$_6$)alkyl)$_2$amino, morpholino, thiomorpholino, piperidino, pyrrolidino, N-acylpiperazino, N-((C$_1$–C$_6$)alkyl)piperazino, N-((C$_6$–C$_{10}$)aryl)piperazino, N-((C$_5$–C$_9$)heteroaryl)piperazino,N-((C$_6$–C$_{10}$)aryl(C$_1$–C$_6$)alkyl)piperazino, N-((C$_5$–C$_9$)heteroaryl(C$_1$–C$_6$)alkyl)piperazino, (C$_1$–C$_6$)alkylthio, sulfinyl or sulfoxyl.

2. A compound according to claim 1 wherein Y is CH$_2$.

3. A compound according to claim 1 wherein X is CH$_2$.

4. A compound according to claim 1 wherein R$^1$ is 1,3-dioxo-1,3-dihydrobenzoisoindolyl.

5. A compound according to claim 1 wherein R$^3$ is methyl.

6. The compound of claim 1 selected from the group consisting of 4-(1,3-dioxo-1,3-dihydrobenzo[f]isoindol-2-yl)-2-{1-[2-(4-methoxyphenyl)-1-(methylcarbamoyl)ethylcarbamoyl]cyclohexylmethyl}butyric acid, 4(1,3-dioxo-5-methoxy-1,3-dihydroisoindol-2-yl)-2-{1-[2-(4-methoxyphenyl)-1-(methylcarbamoyl)ethylcarbamoyl]cyclohexylmethyl}butyric acid, and 4-(1,3-dioxo-5-propoxy-1,3-dihydroisoindol-2-yl)-2-{1-[2-(4-methoxyphenyl)-1-(methylcarbamoyl)ethylcarbamoyl]cyclohexylmethyl}butyric acid.

7. The compound of claim 1 selected from the group consisting of 4-(1,3-dioxo-1,3-dihydro-2H-benzo[f]isoindol-2-yl)-2-{1-[1-(methylcarbamoyl)-2-phenylethylcarbamoyl]cyclohexylmethyl}butyric acid, 4-(1,3dioxo-1,3-dihydro-2H-benzo[f]isoindol-2-yl)-2-{1-[2-(4-methoxypheny)-1-(methylcarbamoyl)ethylcarbamoyl]cyclohexylaminol}butyric acid, 4-(1,3-dioxo-1,3-dihydro-2H-benzo[f]isoindol-2-yl)-2-{1-[2-(4-methoxypheny)-1-(phenylcarbamoyl)ethylcarbamoyl]cyclohexylmethyl}butyric acid, 2-{1-[2,2-dimethyl-1-(methylcarbamoyl)propylcarbamoyl]cyclohexylmethyl}-4-(1,3-dioxo-1,3-dihydro-2H-benzo[f]isoindol-2-yl)butyric acid, 2-{4,4-difluoro-1-[2-(4-methoxyphenyl)-1-(methylcarbamoyl)ethylcarbamoyl]cyclohexylmethyl}-4-

(1,3-dioxo-1,3-dihydro-2H-benzo[f]isoindol-2-yl)butyric acid, 2-{1-[2,2-dimethyl-1-(methylcarbamoyl) propylcarbamoyl]cyclohexylamino}4-(1,3-dioxo-1,3-dihydro-2H-benzo[f]isoindol-2-yl)butyricacid,4-(5,7-dioxo-5,7-dihydro-[1,3]-dioxolo[4,5-f]isoindol6-yl)-2-{1-[1-(methylcarbamoyl)-2-phenylethylcarbamoyl] cyclohexylmethyl}butyricacid, and 4(5,7-dioxo-5,7-dihydro-[1,3]-dioxolo[4,5-f]isoindol-6-yl)-2-{1-[1-(methylcarbamoyl)-2-phenylethylcarbamoyl] cyclohexylamino}butyric acid.

8. A pharmaceutical composition for the treatment of a condition selected from the group consisting of arthritis, cancer, tissue ulceration, restenosis, periodontal disease, epidermolysis bullosa and scleritis charaterized by metalloproteinase activity comprising an effective amount of a compound of claim 1 or a pharmaceutically acceptable salt thereof and a pharmaceutically acceptable carrier.

9. A pharmaceutical composition for the inhibition of matrix metalloproteinases in a mammal comprising a therapeutically effective amount of a compound of claim 1 or a pharmaceutically acceptable salt thereof and a pharmaceutically acceptable carrier.

10. A method of inhibiting matrix metalloproteinases in a mammal comprising administering to said mammal a matrix metalloproteinase inhibiting amount of a compound of claim 1 or a pharmaceutically acceptable salt thereof.

11. A method of treating a condition selected from the group consisting of arthritis, cancer, tissue ulceration restenosis, periodontal disease, epidermolysisbullosa, and scleritis characterized by matrix metalloproteinase activity in a mammal in need thereof comprising admistering to said mammals a therapeutically effective amount of a compound of claim 1 or a pharmaceutically acceptable salt thereof.

* * * * *